United States Patent
Wade et al.

(10) Patent No.: US 9,867,547 B2
(45) Date of Patent: Jan. 16, 2018

(54) SYSTEM AND METHOD TO CALCULATE CARDIAC CHARACTERISTICS

(71) Applicants: Harold James Wade, Rockford, IL (US); Hongxaun Zhang, Palatine, IL (US); Anthony Lawrence, Hoffman Estates, IL (US)

(72) Inventors: Harold James Wade, Rockford, IL (US); Hongxaun Zhang, Palatine, IL (US); Anthony Lawrence, Hoffman Estates, IL (US)

(73) Assignee: Siemens Healthcare GmbH (DE)

( * ) Notice: Subject to any disclaimer, the term of this patent is extended or adjusted under 35 U.S.C. 154(b) by 891 days.

(21) Appl. No.: 14/083,480

(22) Filed: Nov. 19, 2013

(65) Prior Publication Data

US 2014/0148712 A1 May 29, 2014

Related U.S. Application Data

(60) Provisional application No. 61/731,018, filed on Nov. 29, 2012.

(51) Int. Cl.
*A61B 5/021* (2006.01)
*A61B 5/053* (2006.01)

(52) U.S. Cl.
CPC ............ *A61B 5/021* (2013.01); *A61B 5/0535* (2013.01); *A61B 5/0538* (2013.01)

(58) Field of Classification Search
None
See application file for complete search history.

(56) References Cited

U.S. PATENT DOCUMENTS

| | | | |
|---|---|---|---|
| 5,199,438 A * | 4/1993 | Pearlman | A61B 5/02028 600/483 |
| 5,385,156 A | 1/1995 | Oliva | |
| 5,772,601 A * | 6/1998 | Oka | A61B 5/02028 600/495 |
| 7,062,322 B2 | 6/2006 | Stadler et al. | |
| 7,123,954 B2 | 10/2006 | Narayan et al. | |
| 7,189,202 B2 | 3/2007 | Lau et al. | |
| 7,276,022 B2 | 10/2007 | Lau et al. | |
| 7,314,451 B2 | 1/2008 | Halperin et al. | |
| 7,676,266 B1 | 3/2010 | Kroll | |
| 7,720,529 B1 | 5/2010 | Schecter | |
| 7,731,649 B2 | 6/2010 | Ferrazzi | |

(Continued)

OTHER PUBLICATIONS

Boutin, Christine, et al. "Rapid two-stage arterial switch operation. Acquisition of left ventricular mass after pulmonary artery banding in infants with transposition of the great arteries." Circulation 90.3 (1994): 1304-1309.*

(Continued)

*Primary Examiner* — Jacqueline Cheng
*Assistant Examiner* — Jairo Portillo (57) ABSTRACT

A system and method includes reception of a hemodynamic signal, reception of a cardiac impedance signal, identification of a first peak and a second peak of the cardiac impedance signal, identification of a first portion of the hemodynamic signal based on the first peak and a second portion of the hemodynamic signal based on the second peak, and calculation of a cardiac characteristic based on the first portion and the second portion of the hemodynamic signal.

16 Claims, 7 Drawing Sheets

(56) References Cited

U.S. PATENT DOCUMENTS

| | | | | |
|---|---|---|---|---|
| 7,805,194 B1* | 9/2010 | Schecter | ............. | A61N 1/3627 |
| | | | | 607/17 |
| 7,846,426 B2 | 12/2010 | Metzger et al. | | |
| 7,862,513 B2 | 1/2011 | Eigler et al. | | |
| 8,050,757 B2 | 11/2011 | Hsu | | |
| 8,068,907 B2 | 11/2011 | Mann et al. | | |
| 2005/0042589 A1* | 2/2005 | Hatlestad | ............. | A61B 5/0031 |
| | | | | 434/262 |
| 2007/0106162 A1* | 5/2007 | Illyes | ................ | A61B 5/02007 |
| | | | | 600/481 |
| 2010/0022887 A1 | 1/2010 | Main et al. | | |
| 2010/0305637 A1* | 12/2010 | McCabe | ............. | A61B 5/0205 |
| | | | | 607/9 |
| 2011/0066235 A1 | 3/2011 | Ferrazzi | | |
| 2012/0078083 A1 | 3/2012 | McConnell et al. | | |
| 2012/0232417 A1* | 9/2012 | Zhang | ................ | A61N 1/3702 |
| | | | | 600/518 |

OTHER PUBLICATIONS

Deepak Talreja, "Constrictive Pericarditis in the Modern Era", Journal of the American College of Cardiology, vol. 51, No. 3, 2008.

LK Hatle, et al. "Differentiation of constrictive pericarditis and restrictive cardiomyopathy by Doppler echocardiography", Circulation 1989, vol. 79, p. 357-370.

A. Tybjaerg Hansen, et al., "Pressure Curves from the Right Auricle and the Right Ventricle in Chronic Constrictive Pericarditis", Circulation 1951, vol. 3, p. 881-888.

CA Bush, et al., "Occult constrictive pericardial disease. Diagnosis by Rapid volume expansion and correction by pericardiectomy", Circulation 1977, vol. 56, p. 924-930.

\* cited by examiner

SYSTEM AND METHOD TO CALCULATE CARDIAC CHARACTERISTICS

CROSS REFERENCE TO RELATED APPLICATIONS

This application is related to, and claims benefit to and priority of, U.S. Patent Application Ser. No. 61/731,018, filed on Nov. 29, 2012, the contents of which are hereby incorporated by reference in their entirety for all purposes.

BACKGROUND

Field

The embodiments described below relate to the calculation of cardiac characteristics to assist in patient monitoring and/or diagnosis.

Description

The Systolic Area Index (SAI), which is a ratio of right ventricular to left ventricular systolic area during inspiration and expiration, provides a hemodynamic measurement for differentiating between constrictive pericarditis (CP) and restrictive myocardial disease (RMD). Conventional SAI calculations require manual selection of right ventricle to left ventricle pressure curves which temporally correspond to inspiration and to expiration. This selection requires extensive clinical experience and knowledge, and may be inaccurate even if such conditions are present. Inaccurate selection of right ventricle to left ventricle pressure curves results in miscalculation of SAI, which in turn may result in misdiagnosis.

Systems are desired which provide efficient calculation of respiration-dependent cardiac characteristics.

BRIEF DESCRIPTION OF THE DRAWINGS

The construction and usage of embodiments will become readily apparent from consideration of the following specification as illustrated in the accompanying drawings, in which like reference numerals designate like parts, and wherein.

DETAILED DESCRIPTION

The following description is provided to enable any person in the art to make and use the described embodiments and sets forth the best mode contemplated for carrying out the described embodiments. Various modifications, however, will remain readily apparent to those in the art.

Figure 1:
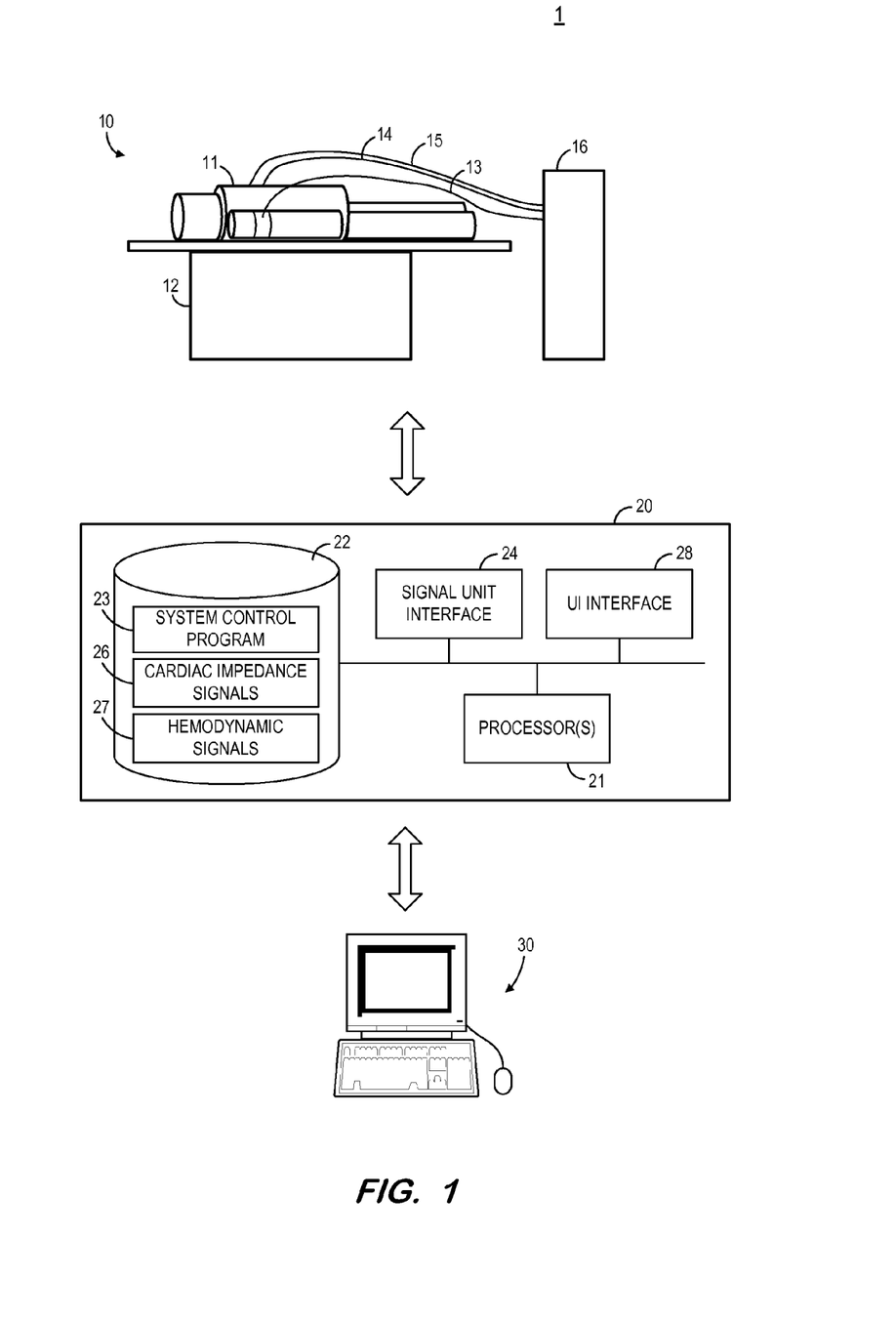
FIG. 1 illustrates a system according to some embodiments.

FIG. 1 illustrates system 1 according to some embodiments. System 1 includes signal acquisition system 10, control and processing system 20, and operator terminal 30. Generally, and according to some embodiments, signal acquisition system 10 acquires a hemodynamic signal and a cardiac impedance signal from patient 11, control and processing system 20 receives signals from signal acquisition system 10 and calculates cardiac characteristics based thereon as described below, and operator terminal 30 displays the cardiac characteristics and any diagnosis derived therefrom.

Signal acquisition system 10 of FIG. 1 consists of patient support (or table) 12, leads 13, 14 and 15, and signal unit 16. According to some embodiments, leads 13 and 14 obtain a cardiac impedance signal indicating time-varying impedance of patient 11 and lead 15 obtains a hemodynamic signal indicating time-varying hemodynamic (e.g., blood pressure) values within patient 11. For example, lead 13 may terminate in a subcutaneous electrode while lead 14 terminates in a heart-implanted electrode. Lead 15 may terminate at a blood pressure monitor attached to an arm of patient 11. Despite the above examples, embodiments may employ any systems for acquiring a cardiac impedance signal and a hemodynamic signal that are or become known.

System 20 may comprise a general-purpose or dedicated computing system. Accordingly, system 20 includes one or more processors 21 configured to execute processor-executable program code to cause system 20 to operate as described herein, and storage device 22 for storing the program code. Storage device 22 may comprise one or more fixed disks, solid-state random access memory, and/or removable media (e.g., a thumb drive) mounted in a corresponding interface (e.g., a USB port).

Storage device 22 stores program code of system control program 23. Storage device 22 also stored signals acquired from system 10 as cardiac impedance signals 26 and hemodynamic signals 27, in any suitable format. One or more processors 21 may execute system control program 23 to control signal unit 16 to acquire the signals, to calculate cardiac characteristics based on the signals as described herein, and to perform any other suitable function. In this regard, system 20 includes signal unit interface 24 for communication with signal unit 16. In some embodiments, system 20 may be directly connected to one or more of leads 13, 14 and 15, eliminating a need for signal unit 16 with respect to the thusly-connected leads.

Terminal 30 may simply comprise a display device and an input device coupled to system 20. In some embodiments, terminal 30 is a separate computing device such as, but not limited to, a desktop computer, a laptop computer, a tablet computer, and a smartphone.

UI interface 28 of system 20 may provide calculated cardiac characteristics and other visualizations to terminal 30. UI interface 28 may receive input entered by an operator into terminal 30, which may be used to change parameters of the processing described herein.

Each of system 10, system 20 and terminal 30 may include other elements which are necessary for the operation thereof, as well as additional elements for providing functions other than those described herein.

According to the illustrated embodiment, system 20 controls the elements of system 10. System 20 also processes signals received from system 10. Embodiments are not limited to a single system performing each of these functions. For example, system 10 may be controlled by a dedicated control system, with the acquired signals being provided to a separate image processing system over a computer network or via a physical storage medium (e.g., a DVD).

Figure 2:
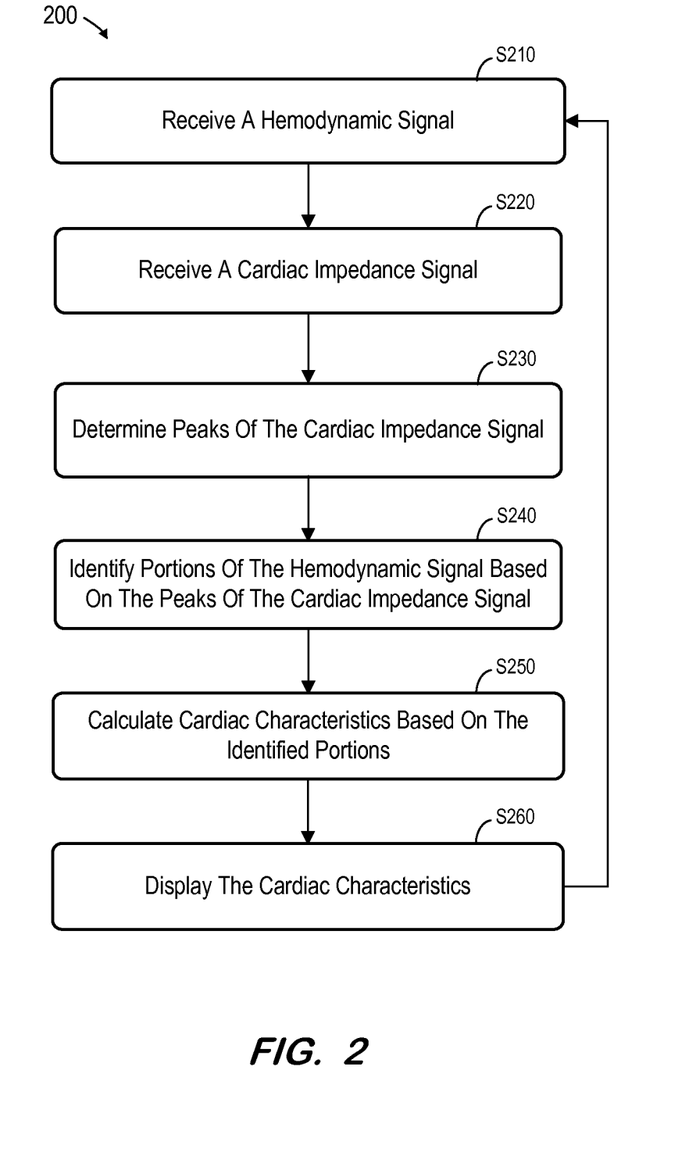
FIG. 2 is a flow diagram of a process according to some embodiments.

FIG. 2 is a flow diagram of process 200 according to some embodiments. Process 200 and the other processes described herein may be performed using any suitable combination of hardware, software or manual means. Software embodying these processes may be stored by any non-transitory tangible medium, including a fixed disk, a floppy disk, a CD, a DVD, a Flash drive, or a magnetic tape. Examples of these processes will be described below with respect to the elements of system 1, but embodiments are not limited thereto.

Initially, at S210, a hemodynamic signal is received. The hemodynamic signal may indicate blood pressure over time within one or more areas of a patient. In some embodiments, the hemodynamic signal indicates right ventricular blood pressure and left ventricular blood pressure. The hemodynamic signal may be acquired from a patient in any manner that is or becomes known, and may be received from an external system. The hemodynamic signal may be received contemporaneously with its acquisition or may be received at a later time (e.g., read from a stored file).

A cardiac impedance signal is received at S220. The cardiac impedance signal provides an indication of the impedance of a patient volume over time. The cardiac impedance signal may also be acquired from a patient in any manner that is or becomes known, and may be received from an external system. The cardiac impedance signal may be received contemporaneously with its acquisition or may be received at a later time. The received hemodynamic signal and cardiac impedance signal are time-stamped or otherwise marked so that they may be temporally synchronized with one another.

One or both of the received signals may be filtered or otherwise processed before or after they are received. For example, the signals may be digitized and band-pass filtered to eliminate low frequency and high frequency noise. Such noise may include power line noise and noise caused by patient movement.

Figure 3:
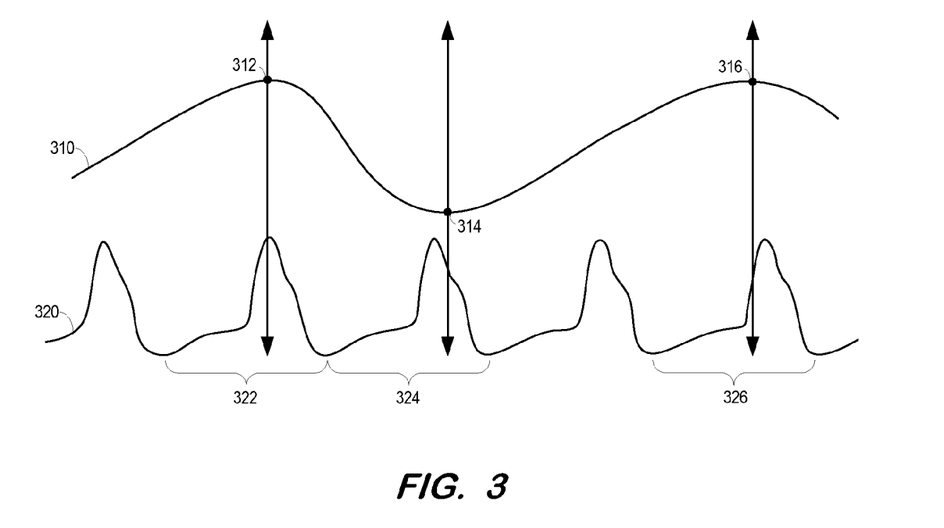
FIG. 3 illustrates identification of portions of a hemodynamic signal according to some embodiments.

For purposes of the present example, FIG. 3 illustrates cardiac impedance signal 310 and hemodynamic signal 320 according to some embodiments. Cardiac impedance signal 310 represents a magnitude of cardiac impedance over time, and hemodynamic signal 320 represents left ventricular blood pressure over time. Hemodynamic signal 320 may also include portions representing right ventricular blood pressure, as will be described below; these portions are omitted from FIG. 3 for clarity.

Peaks of the cardiac impedance signal are determined at S230. The cardiac impedance signal reflects changes in the body's impedance due to respiration over time. Accordingly, the positive and negative peaks of the cardiac impedance signal represent maximum expiration and inspiration, respectively.

Peaks 312, 314 and 316 of signal 310 are identified at S230, with peaks 312 and 316 being positive peaks and peak 314 being a negative peak. In the present example, positive peaks 312 and 316 correspond a time of peak patient expiration and negative peak 314 corresponds to a time of peak patient inspiration.

Next, at S240, portions of the received hemodynamic signal are identified. The portions are identified based on the peaks of the cardiac impedance signal determined at S230. According to some embodiments, one hemodynamic cycle of the hemodynamic signal is identified per impedance signal peak. For a given impedance signal peak, the identified cycle is a cycle which exhibits a peak substantially contemporaneous with the given impedance signal peak. FIG. 3 illustrates identification of portions 322, 324 and 326 based on respective peaks 312, 314 and 316.

Additional methods for identifying portions of the hemodynamic signal based on the peaks of the cardiac impedance signal are described below. Moreover, the portions identified at S240 may be any portions suitable for the cardiac characteristic calculation employed at S250.

Cardiac characteristics are calculated at S250 based on the identified portions of the hemodynamic signal. The calculation at S250 may comprise a calculation of a Systolic Area Index as is known in the art. Conventionally, the Systolic Area Index is calculated as the ratio of the right ventricular to left ventricular systolic pressure-time area during inspiration versus expiration.

Figure 4:
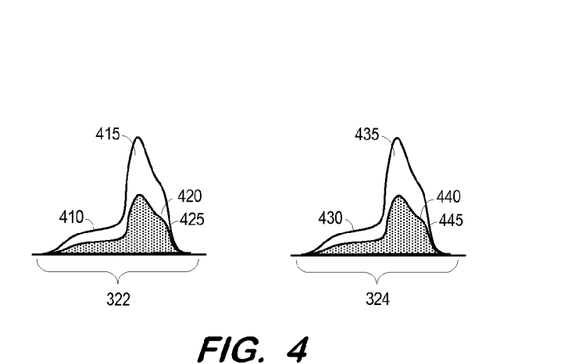
FIG. 4 illustrates an identified portion of a hemodynamic signal according to some embodiments.

FIG. 4 illustrates identified portions 322 and 324 of signal 320. As described above, portion 322 is associated with expiration and portion 324 is associated with inspiration. Portion 322 includes segment 410 representing left ventricular blood pressure and segment 420 representing right ventricular blood pressure. The calculation at S250 may comprise calculating a first ratio of area 445 to area 435, and a second ratio of area 425 to area 415. The first ratio is then divided by the second ratio to produce a Systolic Area Index. Embodiments are not limited to calculation of a Systolic Area Index or any variation thereof. Additional calculations of cardiac characteristics according to some embodiments will be described herein.

The cardiac characteristics are displayed at S260. Prior to S260, a medical diagnosis (e.g., Constrictive Pericarditis) may be determined based on the calculated cardiac characteristics as is known in the art. In such a case, the medical diagnosis may also be displayed at S260.

Figure 5:
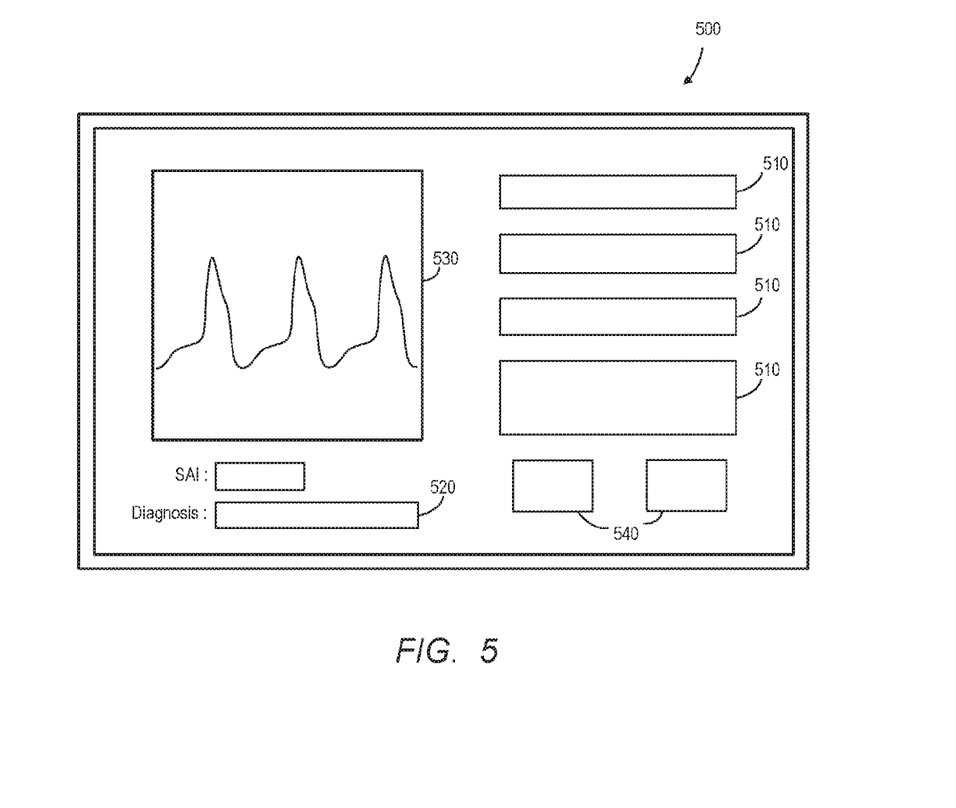
FIG. 5 illustrates a user interface according to some embodiments.

FIG. 5 illustrates interface 500 for displaying a plurality of sequential x-ray difference images according to some embodiments. Interface 500 may be displayed by a display device of terminal 30 in response to execution of program code of system control program 23 by processor(s) 21.

Interface 500 includes area 510 for displaying the calculated cardiac characteristics, and also includes area 520 for displaying any diagnosis determined based on the calculated cardiac characteristics. According to the illustrated embodiment, area 530 displays a hemodynamic signal based on which the cardiac characteristics were calculated. Areas 540 are provided for displaying any suitable information that is or becomes known, such as, but not limited to, signal acquisition parameters, patient biometric data, or the like.

Areas 540 may also or alternatively include one or more user interface controls. These controls may allow an operator to change parameters based on which the received signals are filtered, the portions of a hemodynamic signal are identified, and/or the cardiac characteristics are calculated. Embodiments are not limited to the content and arrangement discussed above with respect to FIG. 5.

Flow may return from S260 to S210 in order to repeat the above-described process and thereby calculate and display updated cardiac characteristics. Substantially real-time monitoring may therefore be provided.

Figure 6:
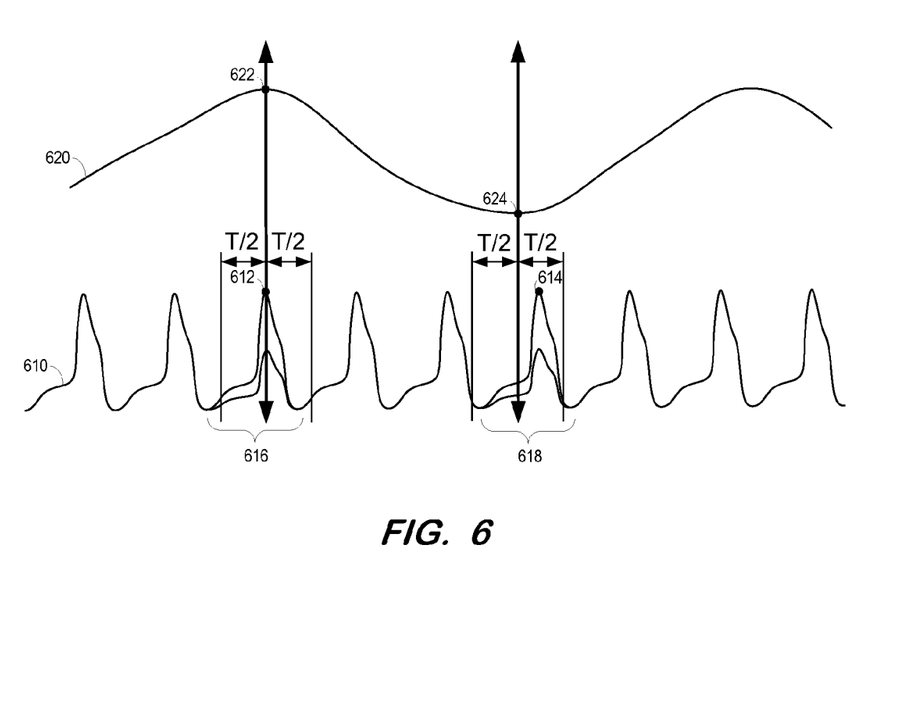
FIG. 6 illustrates identification of portions of a hemodynamic signal according to some embodiments.

FIG. 6 illustrates a method for identifying portions of the hemodynamic signal according to some embodiments of S240. In particular, peaks 622 and 624 of cardiac impedance signal 620 have been determined at S230. At S240, peaks 612 and 614 of hemodynamic signal 610 are identified because they occur within a predetermined time period (i.e., T) from the occurrences of peaks 622 and 624. Then, portion 616 is identified as a full cycle including peak 612 and portion 618 is identified as a full heart cycle including peak 614.

The predetermined time period of FIG. 6 is T/2, one-half of the cardiac cycle length. Embodiments are not limited to this time period. Moreover, the time period may be adjustable by an operator during real-time execution of process 200, for example via user interface controls of interface 500. The time period associated with expiration peaks may differ from the time period associated with inspiration peaks.

Figure 7A:
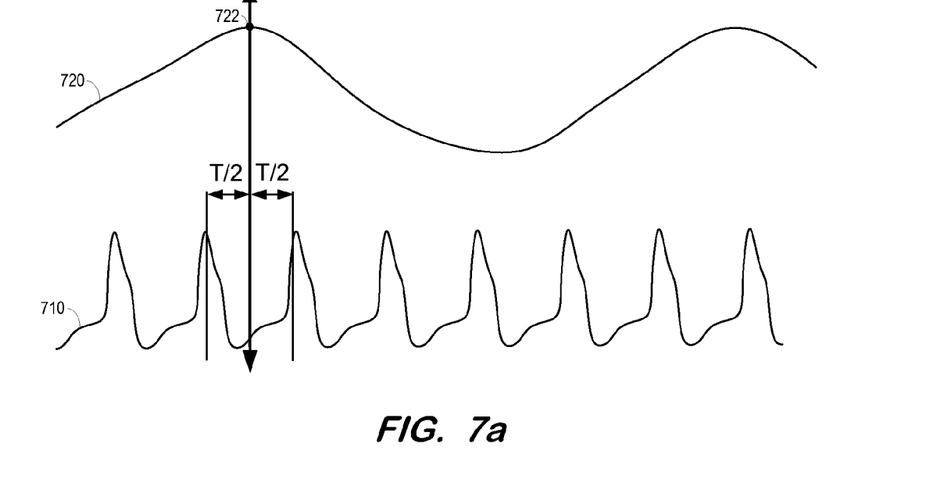
FIGS. 7a and 7b illustrate identification of portions of a hemodynamic signal according to some embodiments.
Figure 7B:
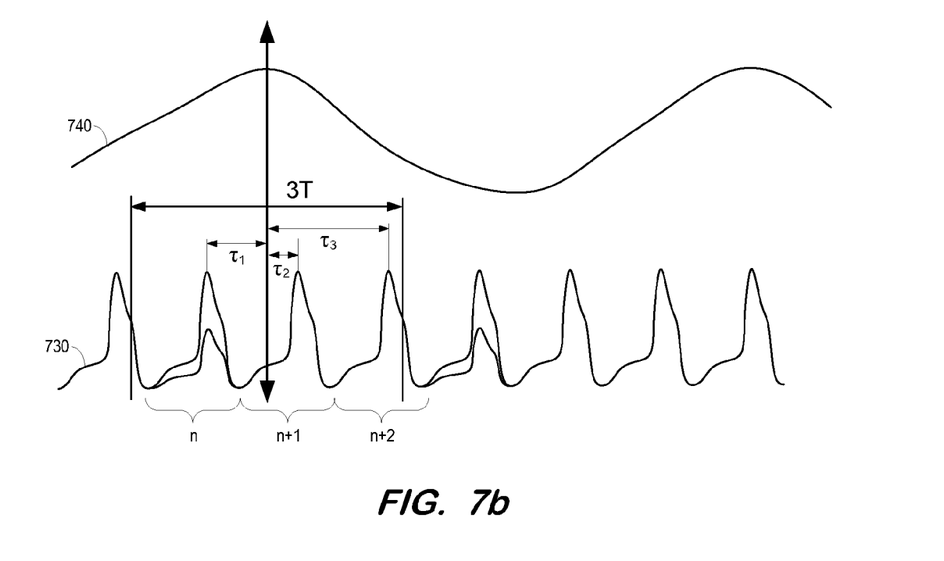

FIG. 7a illustrates an instance in which no peaks of hemodynamic signal 710 occur within the predetermined time period T/2 of peak 722 of cardiac impedance signal 720. Accordingly, to address this situation and/or to provide an improved signal-to-noise ratio, S240 may employ an adaptive multi-cycle detection window as shown in FIG. 7b.

As shown, the predetermined time period (i.e., detection window) is 3T, and three peaks of hemodynamic signal 730 occur within the detection window. $\tau_i$ is the time interval between the center of the detection window and peak i of hemodynamic signal 730. $\tau_i$ may be used as a coefficient or weight for averaging the three hemodynamic cycles which are associated with the peaks of hemodynamic signal 730 occurring within the detection window, as follows:

$$\text{Derived cycle} = \frac{1}{M} \sum_{n=1,\ldots,M} \alpha_n \cdot \text{Cycle}(n),$$

The resulting single derived hemodynamic cycle is then used for the cardiac calculations at S250. M is the total number of cardiac heart cycles inside the detection window, and $\alpha_n$ is a coefficient and weight for corresponding cardiac cycle Cycle (n). The coefficient $\alpha_n$ may be adaptively controlled, and derived linearly or non-linearly (e.g., using an artificial neural network estimation). In some embodiments:

$$\alpha_i = \frac{\left(\sum_{j \in M} \tau_j\right) - \tau_i}{2 \cdot \left(\sum_{j \in M} \tau_j\right)}$$

in which $\tau_i$ and $\tau_j$ is the time duration from the center to the peak of the corresponding heart cycle which also corresponds to the coefficient $\alpha_i$, and M is the total number of cardiac heart cycles inside the detection window.

A description of one possible cardiac characteristic calculation to be performed at S250 was provided above. FIGS. 8a through 8e illustrate other cardiac characteristic calculations which may be performed in some embodiments. Embodiments are not limited to the calculations described herein, or to SAI-related calculations. Rather, embodiments may calculate any cardiac characteristic using any formula based on any portion of a hemodynamic signal.

Figure 8A:
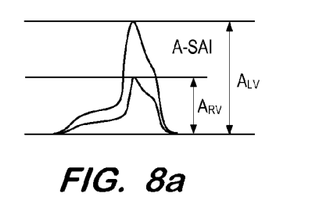
FIGS. 8a through 8e illustrate calculation of cardiac characteristics based on identified portions of a hemodynamic signal according to some embodiments.

FIG. 8a illustrates calculation of an Amplitude systolic index (A-SAI) according to the following equation:

$$A\text{-}SAI = \frac{A_{LV}}{A_{RV}}$$

where $A_{LV}$ and $A_{RV}$ are the maximum amplitude of the left ventricular and the right ventricular segments, respectively, of an identified portion of a hemodynamic cycle.

Figure 8B:
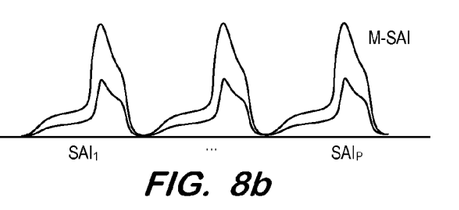

FIG. 8b illustrates calculation of a Multiple heart cycles-based systolic index (M-SAI) according to the following equation:

$$M\text{-}SAI = \Sigma_{i \in \text{shifting window}} \, _T A\text{-}SAI_i$$

where A-SAI$_i$ is any selected SAI-based index, although shown as the Amplitude systolic index (A-SAI) in the present example, and i is the index for the heart cycle of the identified portion of a hemodynamic cycle.

Figure 8C:
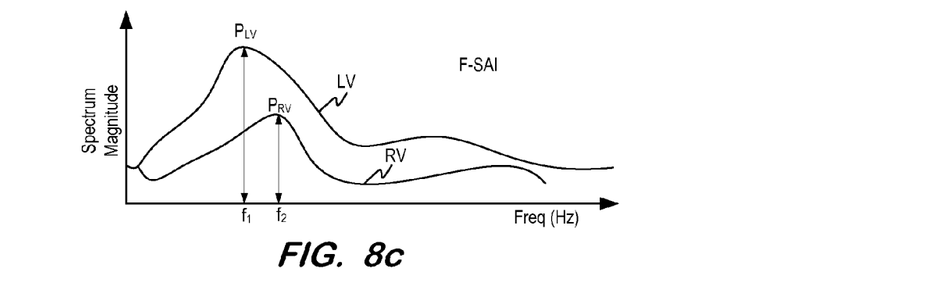

FIG. 8c illustrates values used during calculation of a Frequency and dominant frequency-based systolic index (F-SAI) at S250. The formulas below show three different versions of an F-SAI calculation:

$$F\text{-}SAI \text{ (dominant frequency)} = \frac{P_{LV}}{P_{RV}}$$

$$F\text{-}SAI \text{ (ROI frequency bandwidth spectrum)} = \frac{\sum_{i \in f_1 - f_2} f_{LV}(i)}{\sum_{i \in f_1 - f_2} f_{RV}(i)}$$

$$F\text{-}SAI \text{ (ROI frequency bandwidth energy)} = \frac{\sum_{i \in f_1 - f_2} |f_{LV}(i)|^2}{\sum_{i \in f_1 - f_2} |f_{RV}(i)|^2}$$

where $P_L$ and $P_V$ represent the dominant frequency in the cardiac functional cycle, $f_{LV}(i)$ and $f_{RV}(i)$ represent the spectrum frequency point magnitude or amplitude in the ROI frequency bandwidth area, such as from f1 to f2. Calculation of F-SAI may be particularly advantageous in reducing a noise signal with known noise from the patient or environment, such as 60 Hz noise.

Figure 8D:
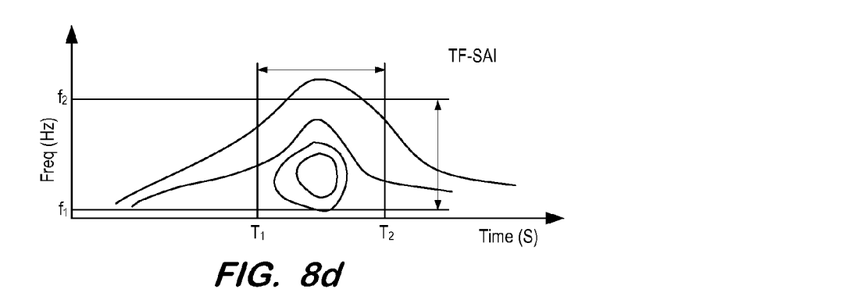

FIG. 8d illustrates calculation of a Time-frequency distribution-based systolic index (TF-SAI), based on the following formula:

$$TF\text{-}SAI \text{ (ROI T-F area)} = \frac{\sum_{i \in \theta} TF_{LV}(i)}{\sum_{i \in \theta} TF_{RV}(i)}$$

TF-SAI may be calculated over a predetermined time and frequency bandwidth. In a clinical application, an ROI area is selected for calculation, such as time interval from T1 to T2 and frequency band from f1 to f2, as shown. TF$_{LV}$(i) and TF$_{RV}$(i) represent the magnitude of a corresponding time-frequency point, and θ is the ROI area in the T-F domain.

Figure 8E:
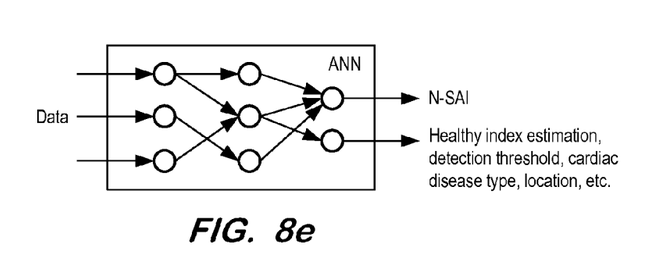

The calculation at S250 may include non-linear methods, such as Fuzzy analysis, expert system estimation, etc. An artificial neural network (ANN) method may be utilized to estimate a systolic index, termed N-SAI. The input of the ANN comprises an identified heart cycle (i.e., a portion of a hemodynamic signal) and parameters such as amplitude, frequency, energy and area. The output of the ANN is an N-SAI index and a derived index which may be used for differentiation and characterization of specific cardiac diseases.

Those in the art will appreciate that various adaptations and modifications of the above-described embodiments can be configured without departing from the scope and spirit of the claims. Therefore, it is to be understood that the claims may be practiced other than as specifically described herein.

What is claimed is:

1. A system comprising;
a signal acquisition system including an interface configured to:
receive a hemodynamic signal; and
receive a cardiac impedance signal; and
a processor configured to execute a system control program in a memory, the system control program causing the processor to:
identify by the processor a first peak and a second peak of the cardiac impedance signal;
identify by the processor a first portion of the hemodynamic signal corresponding to a full heart cycle based on the cardiac impedance signal first peak;
identify by the processor a second portion of the hemodynamic signal corresponding to the full heart cycle based on the cardiac impedance signal second peak;
calculate a systolic area index (SAI) cardiac characteristic based on the first portion and the second portion of the hemodynamic signal;
the identification of the first portion of the hemodynamic signal including causing the processor to:
employ an adaptive multi-cycle detection window by identifying at least two complete periods of the hemodynamic signal occurring within a predetermined time period, wherein the predetermined timed period is centered around the first peak of the cardiac impedance signal;
create a weighted average of the at least two complete periods of the hemodynamic signal with adaptively controlled coefficients, wherein the adaptively controlled coefficients represent a time interval between a center of the multi-cycle detection window and a peak of the hemodynamic signal for each of the at least two complete periods of the hemodynamic signal, wherein the weighted average acts as a derived hemodynamic cycle;
the calculation of the SAI cardiac characteristic based on the derived hemodynamic cycle;
determine a medical diagnosis based on the calculated SAI cardiac characteristic; and
display on an operator terminal at least one of the medical diagnosis determined by the processor and the SAI cardiac characteristic calculated by the processor.

2. The system according to claim 1, wherein the first peak corresponds to patient expiration and the second peak corresponds to patient inspiration.

3. The system according to claim 1, the identification of the first portion of the hemodynamic signal comprises identification of a first peak of the hemodynamic signal occurring within a predetermined time period from the occurrence of the first peak of the cardiac impedance signal.

4. The system according to claim 3, the first peak of the cardiac impedance signal is a positive peak, and the second peak of the cardiac impedance signal is a negative peak, and
the identification of the second portion of the hemodynamic signal comprises identification of a second peak of the hemodynamic signal occurring within a predetermined time period from the occurrence of the second peak of the cardiac impedance signal.

5. The system according to claim 1, wherein the first peak of the cardiac impedance signal is a positive peak, and the second peak of the cardiac impedance signal is a negative peak,
the identification of the second portion of the hemodynamic signal including causing the processor to:
employ a second adaptive multi-cycle detection window by identifying a second at least two complete periods of the hemodynamic signal occurring within a second predetermined time period, wherein the second predetermined timed period is centered around the second peak of the cardiac impedance signal;
create a second weighted average of the second at least two completer periods of the hemodynamic signal with second adaptively controlled coefficients, wherein the second adaptively controlled coefficients represent a time interval between a center of the second multi-cycle detection window and a peak of the hemodynamic signal, wherein the second weighted average act as a second derived hemodynamic cycle;
the calculation, of the SAI cardiac characteristic based on the second derived hemodynamic cycle.

6. The system according to claim 1, wherein the cardiac characteristic is an Amplitude systolic index (A-SAI) calculated according to:

$$A\text{-}SAI = \frac{A_{LV}}{A_{RV}}$$

wherein ALV is a maximum amplitude of a left ventricular segment and ARV is a maximum amplitude of a right ventricular segment of the identified portions of the hemodynamic cycle.

7. The system according to claim 1, wherein the cardiac characteristic is a Multiple heart cycles-based systolic index (M-SAI) calculated according to:

$$\text{M-SAI} = \Sigma_{i \in shifting\ window}\ _TSAI_i$$

wherein SAIi is a Systolic Area Index, and i is an index for a heart cycle of the identified portions of the hemodynamic cycle.

8. The system according to claim 1, wherein the cardiac characteristic is a frequency-based Systolic Area Index (F-SAI), and is calculated based on a spectrum frequency point magnitude or amplitude in a frequency band of interest.

9. A method comprising:
receiving a hemodynamic signal at a processor configured to execute system control program instructions;
receiving a cardiac impedance signal at the processor;
identifying by the processor a first peak and a second peak of the cardiac impedance signal;
identifying by the processor a first portion of the hemodynamic signal corresponding to a full heart cycle based on the first cardiac impedance signal peak;
identifying by the processor a second portion of the hemodynamic signal corresponding to the full heart cycle based on the second cardiac impedance signal peak;
calculating a systolic area index (SAI) cardiac characteristic based on the first portion and the second portion of the hemodynamic signal;
the identification of the first portion of the hemodynamic signal including:
employing an adaptive multi-cycle detection window by the processor identifying at least two complete periods of the hemodynamic signal occurring within a predetermined time period, wherein the predetermined timed period is centered around the first peak of the cardiac impedance signal;

creating, by the processor, a weighted average of the at least two complete periods of the hemodynamic signal with an adaptively controlled coefficients, wherein the adaptively controlled coefficients represent a time interval between a center of the multi-cycle detection window and a peak of the hemodynamic signal for each of the at least two complete periods of the hemodynamic signal, wherein the weighted average acts as a derived hemodynamic cycle;

the calculation of the SAI cardiac characteristic based on the derived hemodynamic cycle;

determining by the processor a medical diagnosis based on the calculated SAI cardiac characteristic; and displaying on an operator terminal at least one of the medical diagnosis determined by the processor and the SAI cardiac characteristic calculated by the processor.

10. The method according to claim 9, wherein the first peak corresponds to patient expiration and the second peak corresponds to patient inspiration.

11. The method according to claim 9, the identifying the first portion of the hemodynamic signal comprises identifying a first peak of the hemodynamic signal occurring within a predetermined time period from the occurrence of the first peak of the cardiac impedance signal.

12. The method according to claim 11, wherein the first peak of the cardiac impedance signal is a positive peak, and the second peak of the cardiac impedance signal is a negative peak, and the identifying the second portion of the hemodynamic signal comprises identifying a second peak of the hemodynamic signal occurring within a predetermined time period from the occurrence of the second peak of the cardiac impedance signal.

13. The method according to claim 9, wherein the first peak of the cardiac impedance signal is a positive peak and the second peak of the cardiac impedance signal is a negative peak, and the identifying the second portion of the hemodynamic signal including:

employing a second adaptive multi-cycle detection window by the processor identifying a second at least two complete periods of the hemodynamic signal occurring within a second predetermined time period, wherein the second predetermined timed period is centered around the second peak of the cardiac impedance signal;

a creating a second weighted average of the second at least two complete periods of the hemodynamic signal with second adaptively controlled coefficients, wherein the second adaptively controlled coefficients represent a time interval between a center of the second multi-cycle detection window and a peak of the hemodynamic signal for each of the second at least two complete periods of the hemodynamic signal, wherein the second weighted average acts as a second derived hemodynamic cycle;

the calculating the SAI cardiac characteristic based on the second derived hemodynamic cycle.

14. The method according to claim 9, wherein the cardiac characteristic is an Amplitude systolic index (A-SAI) calculated according to:

$$A\text{-}SAI = \frac{A_{LV}}{A_{RV}}$$

wherein ALV is a maximum amplitude of a left ventricular segment and ARV is a maximum amplitude of a right ventricular segment of the identified portions of the hemodynamic cycle.

15. The method according to claim 9, wherein the cardiac characteristic is a Multiple heart cycles-based systolic index (M-SAI) calculated according to:

$$M\text{-}SAI = \Sigma_{i \in shifting\ window\ T} SAI_i$$

wherein SAIi is a Systolic Area Index, and i is an index for a heart cycle of the identified portions of the hemodynamic cycle.

16. The method according to claim 9, wherein the cardiac characteristic is a frequency-based Systolic Area Index (F-SAI), and the method includes calculating the F-SAI based on a spectrum frequency point magnitude or amplitude in a frequency band of interest.

* * * * *